United States Patent [19]
Goldmann et al.

[11] Patent Number: 4,721,719
[45] Date of Patent: Jan. 26, 1988

[54] DIHYDROPYRIDINELACTOLS AND THEIR USE AS MEDICAMENTS WHICH INFLUENCE BLOOD SUGAR

[75] Inventors: Siegfried Goldmann; Friedrich Bossert; Hans J. Ahr; Hilmar Bischoff; Walter Puls, all of Wuppertal; Dieter Petzinna, Wesel; Klaus Schlossmann; Joachim Bender, both of Wuppertal, all of Fed. Rep. of Germany

[73] Assignee: Bayer Aktiengesellschaft, Leverkusen, Fed. Rep. of Germany

[21] Appl. No.: 900,866

[22] Filed: Aug. 27, 1986

[30] Foreign Application Priority Data

Jan. 17, 1986 [DE] Fed. Rep. of Germany ....... 3601226

[51] Int. Cl.$^4$ .................. A61K 31/44; C07D 495/04
[52] U.S. Cl. ................................. 514/302; 546/116
[58] Field of Search .................... 546/116; 514/302

[56] References Cited

U.S. PATENT DOCUMENTS 4,647,568 3/1987 Frankowiak et al. ............. 546/116

FOREIGN PATENT DOCUMENTS 0080220 6/1983 European Pat. Off. .

*Primary Examiner*—Henry R. Jiles
*Assistant Examiner*—Bernard I. Dentz
*Attorney, Agent, or Firm*—Sprung Horn Kramer & Woods

[57] ABSTRACT

Reducing blood sugar with the novel dihydropyridinelactols, or salts thereof, of the formula

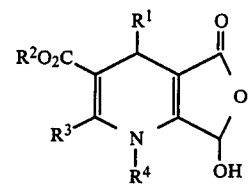

in which
$R^1$ represents a phenyl, naphthyl, thienyl, pyridyl, chromonyl, thiochromonyl or thiochromenyl radical, the stated radicals optionally containing 1 or 2 identical or different substituents from the group consisting of fluorine, chlorine and bromine, alkyl, alkoxy and alkylthio, each having 1 to 6 carbon atoms, and fluoroalkyl or fluoroalkoxy, each having up to 3 carbon atoms and 3 fluorine atoms, and nitro and cyano,
$R^2$ represents a straight-chain, branched or cyclic alkyl having up to 12 carbon atoms which is optionally interrupted by 1 or 2 oxygen or sulphur atoms and which is optionally substituted by fluorine, chlorine, phenyl, cyano, hydroxyl, amino, $C_1$-$C_3$-alkylamino, di-$C_1$-$C_3$-alkylamino or N-benzylmethylamino,
$R^3$ represents cyano or straight-chain or branched alkyl which has up to 4 carbon atoms and is optionally interrupted in the chain by N-$C_1$-$C_3$-alkyl and/or oxygen, and
$R^4$ represents straight-chain, branched or cyclic alkyl which has up to 6 carbon atoms and is optionally interrupted by 1 or 2 oxygen atoms and is substituted by one or more radicals from amongst fluorine, chlorine, hydroxyl, phenyl, amino, carboxyl and $C_1$-$C_4$-alkoxycarbonyl.

11 Claims, No Drawings

DIHYDROPYRIDINELACTOLS AND THEIR USE AS MEDICAMENTS WHICH INFLUENCE BLOOD SUGAR

The invention relates to dihydropyridinelactols, processes for their preparation, and their use in medicaments, in particular of medicaments which influence blood sugar.

The present invention relates to dihydropyridinelactols of the general formula I,

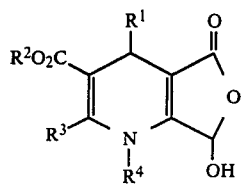

in which
$R^1$ represents a phenyl, naphthyl, thienyl, pyridyl, chromonyl, thiochromonyl or thiochromenyl radical, the stated radicals optionally containing 1 or 2 identical or different substituents from the group comprising fluorine, chlorine and bromine, alkyl, alkoxy and alkylthio, each having 1 to 6 carbon atoms, and fluoroalkyl or fluoroalkoxy, each having up to 3 carbon atoms and 3 fluorine atoms, and nitro and cyano,
$R^2$ represents a straight-chain, branched or cyclic alkyl having up to 12 carbon atoms which is optionally interrupted by 1 or 2 oxygen or sulphur atoms and which is optionally substituted by fluorine, chlorine, phenyl, cyano, hydroxyl, amino, $C_1$-$C_3$-alkylamino, di-$C_1$-$C_1$-alkylamino or N-benzylmethylamino,
$R^3$ represents cyano or straight-chain or branched alkyl which has up to 4 carbon atoms and is optionally interrupted in the chain by N-$C_1$-$C_1$-alkyl and/or oxygen, and
$R^4$ represents straight-chain, branched or cyclic alkyl which has up to 6 carbon atoms, is optionally interrupted by 1 or 2 oxygen atoms and is optionally substituted by one or more radicals from amongst fluorine, chlorine, hydroxyl, phenyl, amino, carboxyl and $C_1$-$C_4$-alkoxycarbonyl,
in the form of their isomers, isomer mixtures, optical antipodes or racemates, and their physiologically acceptable able salts.

Preferred compounds of the general formula I which may be mentioned are those in which
$R^1$ represents a phenyl, naphthyl or thienyl radical, the stated radicals optionally containing 1 or 2 identical or different substituents from the group comprising fluorine, chlorine, alkoxy, alkylthio and alkyl, each of which has up to 3 carbon atoms, and trifluoromethyl, nitro and cyano,
$R^2$ represents straight-chain or branched alkyl which has up to 6 carbon atoms, is optionally interrupted by oxygen or sulphur or is substituted by fluorine or phenyl,
$R^3$ represents straight-chain or branched alkyl having up to 3 carbon atoms, and
$R^4$ represents straight-chain, branched or cyclic alkyl which has up to 4 carbon atoms and is optionally substituted by carboxyl or $C_1$-$C_3$-alkoxycarbonyl,
in the form of their isomers, isomer mixtures, optical antipodes or racemates, and their physiologically acceptable salts.

Compounds of the general formula I, in which
$R_1$ represents a phenyl radical which is optionally substituted by nitro, chlorine, trifluoro-$C_1$-$C_1$-alkyl or $C_1$-$C_1$-alkyl,
$R_2$ represents a $C_1$-$C_4$-alkyl radical which is optionally substituted by $C_1$- or $C_2$-alkoxy,
$R_3$ represents a $C_1$-$C_1$-alkyl group, and
$R_4$ represents a $C_1$-$C_4$-alkyl group, may be mentioned in particular.

The compounds according to lhe invention may be present in the form of their salts. The physiogically acceptable salts of the substances according to the invention with inorganic or organic acids are preferred. The following may be mentioned as examples: hydrohalides, hydrogen sulphates, sulphates, hydrogen phosphates, acetates, maleates, citrates, fumarates, tartrates, lactates or benzoates.

The compounds according to the invention exist in stereoisomeric forms which either behave as object and image (enantiomers) or do not behave as object and image (diastereomers). The invention relates both to the antipodes and to the racemic forms and diastereomer mixtures. The racemic forms as well as the diastereomers can be separated into the stereoisomerically pure components in a customary manner (see E. L. Eliel, Stereochemistry of Carbon Compounds McGraw Hill, 1962).

The compounds according to the invention, of the general formula I, are prepared by a process in which
[A]formyl compounds of the general formula (II),

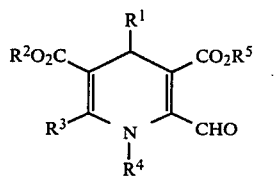

in which
$R^1$-$R^4$ have the stated meaning and
$R^5$ represents sraight-chain or branched alkyl having up to 8 carbon atoms,
in suitable solvents, are first reacted with a base and then with acid, or
[B]dihyropridinelactones of the general formula (III),

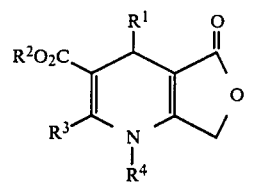

in which $R^1$-$R^4$ have the stated meaning, are brominated in suitable solvents, if appropriate in the presence of a base, and then hydrolyzed or directly hydroxylated.

Depending on the type of starting materials used, preparation of compounds according to the invention by processes A and B can be illustrated by the following equation:

[A]

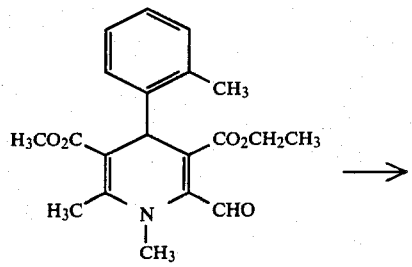

→

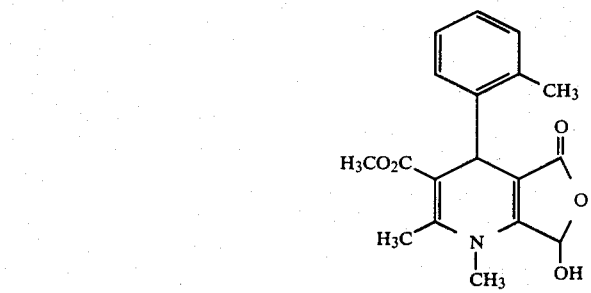

[B]

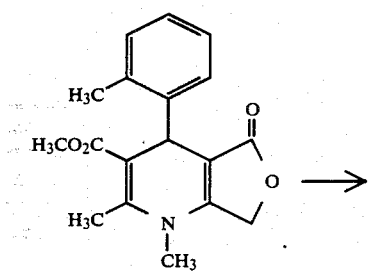

→

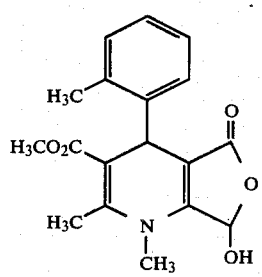

Process A

Suitable solvents for process A are water and all inert organic solvents which do not change under the reaction conditions. These preferably include alcohols, such as methanol, ethanol, propanol or isopropanol, ethers, such as diethyl ether, dioxane, tetrahydrofuran, glycol monomethyl ether or glycol dimethyl ether, acetonitrile, pyridine, dimethylformamide, dimethyl sulphoxide and hexamethylphosphoric acid triamide. It is also possible to use mixtures of the stated solvents.

Suitable bases for process A are the customary inorganic or organic bases. These preferably include alkali metal hydroxides, such as sodium hydroxide or potassium hydroxide, or alkali metal alcoholates, such as sodium methylate, sodium ethylate, potassium ethylate, potassium methylate or potassium tert.-butylate, alkali metals, such as sodium, alkali metal hydrides, such as sodium hydride or potassium hydride, and alkali metal amides, such as sodium amide or lithium diisopropylamide.

Suitable acids are the customary organic or inorganic acids. These preferably include mineral acids, such as hydrochloric acid, hydrobromic acid, sulphuric acid and phosphoric acid, and organic carboxylic acids, such as acetic acid.

Process A is carried out in a manner which is known per se, by first reacting the formyl compounds of the formula (II), in suitable solvents, with 100 to 5 mols, preferably from 50 to 10 mols. of a base per mol of formyl compound and then treating the reaction mixture with acids. Working up is effected in a customary manner familiar to a skilled worker.

The reaction is carried out in general in temperatures from 0° C. to 150° C., preferably from 20° C. to 100° C.

The reaction can be carried out under atmospheric pressure as well as under elevated or reduced pressure. In general, atmospheric pressure is employed.

The starting compounds of the formula (II) are known or can be prepared by known processes (see DOS (German Published Specification) No. 2,629,892).

Process B

Bromination is carried out in a manner which is known per se, with the customary brominating agents, such as N-bromosuccinimide or bromine, preferably with bromine.

Suitable bases are the customary bases. These preferably include alkali metals, such as sodium or potassium, alkali metal hydrides, such as sodium hydride or potassium hydride, alkali metal amides, such as sodium amide or lithium diisopropylamide, and organometallic compounds, such as phenyllithium, n-butyllithium or tert.-butyllithium, and alcoholates, such as Na ethylate and potassium t-butylate.

Suitable solvents are customary inert organic solvents. These preferably include ethers, such as diethyl ether, dioxane or tetrahydrofuran, and hydrocarbons, such as benzene, toluene, xylene, hexane, cyclohexane or oil fractions. It is also possible to employ mixtures of the stated solvents.

The bromination is carried out in a temperature range from −120° C. to 100° C., preferably from −78° C. to 50° C.

The bromination is carried out in such a way that an anion is first produced with 5 to 1 mol, preferably with 2 to 1 mol, particularly preferably with 1 mol, of base per mol of the starting compound (III), and the said anion is converted to bromide by means of bromine. The subsequent conversion of the bromine compound to the corresponding hydroxy compound of the formula (I) is advantageously carried out without isolating the bromine compound. This hydrolysis is carried out in a manner which is known per se, by means of water, if appropriate in the presence of traces of an acid, such as hydrochloric acid or sulphuric acid.

The procedure of process B can be carried out both under atmospheric pressure and under elevated or reduced pressure and is familiar to the skilled worker. In general, atmospheric pressure is employed.

The conversion of the compounds (III) to the compounds (I) according to the invention can, however, also be carried out by other methods known from the literature and is not restricted to the stated methods.

Hydroxylation can also be carried out by means of 2-sulphonyloxaziridine, with molybdenum peroxide/-pyridine/phosphite or with oxygen/phosphite, in each case in the presence of bases, in inert organic solvents, as described, for example, by E. Vedejs in J. Am. Chem. Soc. 96, 5944 (1974) or J. Org. Chem. 43, 188 (1978), or by J. M. Billmers, J. Finn in J. Org. Chem. 49, 3243 (1984) or by H. H. Wassermann, B. H. Lipschutz in Tetrahedron Letters 1975, 1731.

The compounds according to the invention, of the formula I, possess a valuable pharmacological action spectrum.

These compounds reduce the blood sugar level and can therefore be employed for the treatment of diabetes.

The blood glucose-reducing action of the substances to be investigated was tested on male Wistar rats weighing between 140 and 190 g. For this purpose, the rats were weighed 18 hours before administration of the substances, divided into groups of 6 animals and made to fast. The substances to be investigated were suspended in aqueous 0.75% strength tragacanth suspension using an Ultra-Turrax directly before administration. Administration of the tragacanth suspension (control animals) or of the substances suspended in tragacanth was effected by means of a gavage.

For each rat, blood was withdrawn from the retroorbital venous plexus 30, 60 and 120 minutes after administration. In each case, 30 µl of blood were withdrawn using an automatic dilutor, and were deproteinized with 0.3 ml of uranyl acetate (0.16%). After centrifuging, the glucose in the supernatant liquid was determined photometrically by the glucose oxidase method in a Gemsaec solids analyser, using 4-amino-phenazone as the color reagent. The results were evaluated using the Student t-test, $p < 0.05$ being chosen as the significance limit.

Substances which at some time produced a significant reduction in the blood glucose concentration of rats, by at least 10%, compared with the control group, which received only tragacanth suspension, were stated to be effective.

Table 1 below contains the changes found in the blood glucose concentrations, as a percentage of the control.

TABLE 1

| Substance (Example No.) | Decrease in blood glucose concentration as a % of the control 10 mg/kg p.o. |
| --- | --- |
| 1 | 29 |
| 2 | 34 |

The present invention includes pharmaceutical formulations which, in addition to non-toxic, inert pharmaceutically suitable excipients, contain one or more active compounds according to the invention, or which consist of one or more active compounds according to the invention, as well as processes for the preparation of these formulations.

The present invention also includes pharmaceutical formulations in dosage units. This means that the formulations are in the form of individual parts, for example tablets, dragees, capsules, pills, suppositories and ampules of which the content of active compound correspond to a fraction or a multiple of an individual dose. The dosage units can contain, for example, 1, 2, 3 or 4 individual doses or ½, ⅓, or ¼ of an individual dose. An individual dose preferably contains the amount of active compound which is given in one administration and which usually corresponds to a whole, a half, a third or a quarter of a daily dose.

By non-toxic, inert pharmaceutically suitable excipients there are to be understood solid, semi-solid or liquid diluents, fillers and formulation auxiliaries of every kind.

Tablets, dragees, capsules, pills, granules, suppositories, solutions, suspensions and emulsions may be mentioned as preferred pharmaceutical formulations.

Tablets, dragees, capsules, pills and granules can contain the active compound or compounds alongside the customary excipients, such as (a) fillers and extenders, for example starch, lactose, sucrose, glucose, mannitol and silica, (b) binders, for example carboxymethylcellulose, alginates, gelatine and polyvinylpyrrolidone, (c) humectants, for example glycerol, (d) disintegrating agents, for example agar-agar, calcium carbonate and sodium bicarbonate, (e) solution retarders, for example paraffin, and (f) resorption accelerators, for example quaternary ammonium compounds, (g) wetting agents, for example cetyl alcohol and glycerol monostearate, (h) adsorbents, for example kaolin and betonite, and (i) lubricants, for example talc, calcium stearate and magnesium stearate and solid polyethylene glycols, or mixtures of the compounds listed under (a) to (i).

The tablets, dragees, capsules, pills and granules can be provided with the customary coatings and shells, optionally containing opacifying agents, and can also be of such composition that they release the active compound or compounds only, or preferentially, in a certain part of the intestinal tract, optionally in a delayed manner, examples of embedding compositions which can be used being polymeric substances and waxes.

The active compound or compounds, optionally together with one or more of the abovementioned excipients, can also be in a micro-encapsulated form.

Suppositories can contain, in addition to the active compound or compounds, the customary water-soluble or water-insoluble excipients, for example polyethylene glycols, fats, for example cocoa fat, and higher esters (for example $C_{14}$-alcohol with $C_{16}$-fatty acid), or mixtures of these substances.

Solutions and emulsions can contain, in addition to the active compound or compounds, the customary excipients, such as solvents, solubilizing agents and emulsifiers, for example water, ethyl alcohol, isopropyl alcohol, ethyl carbonate, ethyl acetate, benzyl alcohol, benzyl benzoate, propylene glycol, 1,3-butylene glycol, dimethylformamide, oils, especially cottonseed oil, groundnut oil, maize germ oil, olive oil, castor oil and sesame oil, glycerol, glycerol-formal, tetrahydrofurfuryl alcohol, polyethylene glycols and fatty acid esters of sorbitan, or mixtures of these substances.

For parenteral administration, the solutions and emulsions can also be in a sterile form which is isotonic with blood.

Suspensions can contain, in addition to the active compound or compounds, the customary excipients, such as liquid diluents, for example water, ethyl alcohol or propylene glycol, suspending agents, for example ethoxylated isostearyl alcohols, polyoxyethylene sorbitol esters and sorbitan esters, micro-crystalline cellulose, aluminum metahydroxide, bentonite, agar-agar and tragacanth, or mixtures of these substances.

The formulation forms mentioned can also contain colorants, preservatives and additives which improve the odor and flavor, for example peppermint oil and eucalyptus oil, and sweeteners, for example saccharin.

The therapeutically active compounds should preferably be present in the abovementioned pharmaceutical formulations in a concentration of about 0.1 to 99.5, preferably of about 0.5 to 95, % by weight of the total mixture.

The abovementioned pharmaceutical formulations can also contain other pharmaceutical active compounds in addition to the active compounds according to the invention.

The abovementioned pharmaceutical formulations are prepared in the customary manner according to known methods, for example by mixing the active compound or compounds with the excipient or excipients.

The present invention also includes the use of the compounds of the formula I and/or their salts, and of pharmaceutical formulations which contain the compounds of the formula I and/or their salts, in human and veterinary medicine, for the prevention, alleviation and/or cure of the abovementioned diseases.

In general, it has proved advantageous, both in human medicine and in veterinary medicine, to administer the active compound or compounds according to the invention in total amounts of about 0.01 to about 200 mg/kg, preferably 0.1 to 50 mg/kg, of body weight every 24 hours, optionally in the form of several individual administrations, in order to achieve the desired results.

However, it can be necessary to deviate from the dosages mentioned, and in particular to do so as a function of the species and the body weight of the subject to be treated, the nature and severity of the disease, the nature of the formulation and of the administration of the medicament and the time or interval over which the administration takes place. Thus it can in some cases suffice to manage with less than the abovementioned amount of active compound, while in other cases the abovementioned amount of active compound must be exceeded. The particular optimum dosage required and the type of administration of the active compounds can easily be determined by anyone skilled in the art on the basis of his expert knowledge.

EXAMPLE 1

(Process B)

Isopropyl 4-(2-chlorophenyl)-1-ethyl-7-hydroxy-2-methyl-5-oxo-1,4,5,7-tetrahydrofuro[3,4-b]pyridine-3-carboxylate

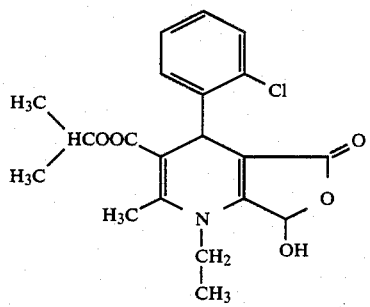

60 mmol of diisopropylamine in 100 ml of analytical grade tetrahydrofuran are initially taken. 50 mmol of butyllithium are added at a temperature of 0°C., under a stream of $N_2$. Thereafter, the mixture is cooled to $-78°$ C. and a solution of 50 mmol of isopropyl 4-(2-chlorophenyl)-1-ethyl-2-methyl-5-oxo-1,4,5,7-tetrahydrofuro[3,4-b]pyridine3-carboxylate (dissolved in THF) is added dropwise. The mixture is stirred for 15 minutes at $-78°$ C., and this solution is pumped, with the aid of nitrogen, into a solution of 50 mmol of $Br_2$ and 50 ml of THF, and immediately thereafter 50 mmol of cyclohexene are added and the mixture is allowed to warm up to room temperature and is evaporated down, the residue is dissolved in DMSO, and $H_2O$ is added until the mixture starts to become cloudy. The mixture is left to stand for 12 hours, and the product is precipitated with $H_2O$, filtered off under suction and separated with 9:1 $CHCl_3$/MeOH over silica gel.

Yield: 30% of theory.

m.p.: 145°–147° C.

The following was prepared analogously to Example 1:

EXAMPLE 2

Ethyl 4-(2-chlorophenyl)-1-ethyl-7-hydroxy-2-methyl-5-oxo-1,4,5,7-tetrahydrofuro[3,4-b]pyridine-3-carboxylate

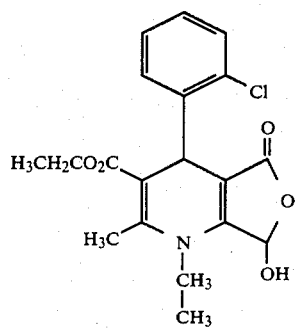

Yield: 13% of theory (amorphous).

MS: 377 (10%. M+); 348 (20%); 304 (10%) 266 (100%); 29 (40%).

EXAMPLE 3

Isopropyl 1-ethyl-7-hydroxy-2-methyl-4-(2-methylphenyl)-5-oxo-1,4,5,7-tetrahydrofuro[3,4-b]pyridine-3-carboxylate

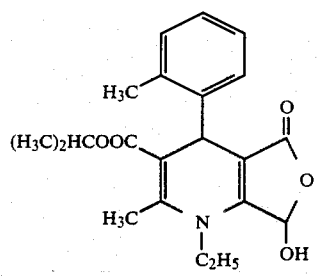

Yield: 30% of theory.

MS:371 (15%, M+); 328 (25%); 280 (80%); 278 (100%); 192 (20%) 164 (20%); 42 (50%); 42 (50%); 20%); 42 (50%); 29 (35%).

EXAMPLE 4

Isopropyl 1-ethyl-7hydroxy-2-methyl-5-oxo-4-(2-trifluoromethyl-phenyl)-1,4,5,7-tetrahydrofuro[3,4-b]pyridine-3-carboxylate

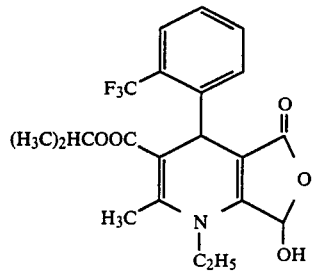

Yield: 35% of theory.

$^1$H-NMR (CDCl$_3$):=0.8 (d, 3H); 1.1 (d, 3H); 1.3 (t, 3H); 2.3 (s, 3H); 3.5–3.9 (s, broad, 2H); 4.8 (hept., 1H); 5.3 (s, 1H); 5.9 (s, 1H); 6.1 (s, broad, 1H); 7.2–7.6 (m, 4H).

EXAMPLE 5

(process A)

Isopropyl 1-ethyl-7-hydroxy-2-methyl-4-(3-nitrophenyL)-5-oxo-1,4,5,7-tetrahydrofuro[3,4-b]-pyridine-3-carboxylate

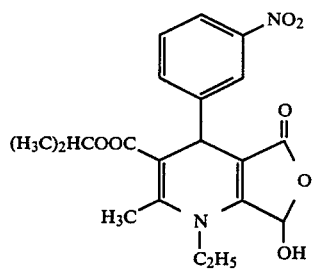

5 mmol of 3-methyl 5-isopropyl-1-ethyl-2-formyl-6-methyl-4-(3-nitrophenyl)-1,4-dihydropyridine-3,5-dicarboxylate in 40 mmol of 2 N KOH are initially taken and heated for a short time at 50° C. in a waterbath, after which stirring is continued for 1 hour at room temperature. The solution is clarified with active carbon and acidified with hydrochloric acid, and the precipitate is filtered off under suction.

Yield: 25% of theory.

$^1$H-NMR (CDCl$_3$):=0.8 (d, 3H); 1.1 (d, 3H); 1.3 (t, 3H); 2.3 (s, 3H; 3.4–4.0 (m, broad, 2H); 4.7 (m, 1H); 5.1 (s, 1H); 5.9 (s, 1H);

6.2 (s, broad, 1H); 7.3–8.3 (m, 4H).

It is understood that the specification and examples are illustrative but not limitative of the present invention and that other embodiments within the spirit and scope of the invention will suggest themselves to those skilled in the art.

We claim:

1. A dihydropyridinelactol of the formula

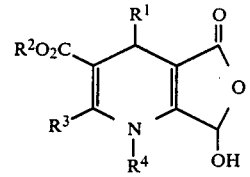

in which $R^1$ represents a phenyl, naphthyl, thienyl, pyridyl, chromonyl, thiochromonyl or thiochromenyl radical, the stated radicals optionally containing 1 or 2 identical or different substituents from the group consisting of fluorine, chlorine and bromine, alkyl, alkoxy and alkylthio, each having 1 to 6 carbon atoms, and fluoroalkyl or fluoroalkoxy, each having up to 3 carbon atoms and 3 fluorine atoms, and nitro and cyano, $R^2$ represents a straight-chain, branched or cyclic alkyl having up to 12 carbon atoms which is optionally interrupted by 1 or 2 oxygen or sulphur atoms and which is optionally substituted by fluorine, chlorine, phenyl, cyano, hydroxyl, amino, $C_1$–$C_3$-alkylamino, di-$C_1$–$C_3$-alkylamino or N-benzylmethylamino, $R^3$ represents cyano or straight-chain or branched alkyl which has up to 4 carbon atoms and is optionally interrupted in the chain by N-$C_1$-$C_1$-alkyl and/or oxygen, $R^4$ represents straight-chain, branched or cyclic alkyl which has up to 6 carbon atoms and is optionally interrupted by 1 or 2 oxygen atoms and is optionally substituted by one or more radicals from amongst fluorine, chlorine, hydroxyl, phenyl, amino, carboxyl and $C_1$-$C_4$-alkoxycarbonyl, or a physiologically acceptable salt thereof.

2. A dihydropyridinelactol according to claim 1 in which $R^1$ represents a phenyl, naphthyl or thienyl radical, the stated radicals optionally containing 1 or 2 identical or different substituents from the group consisting of fluorine, chlorine, alkoxy, alkylthio and alkyl, each of which has up to 3 carbon atoms, and trifluoromethyl, nitro and cyano, $R^2$ represents straight-chain or branched alkyl which has up to 6 carbon atoms, is optionally interrupted by oxygen or sulphur or is substituted by fluorine or phenyl, $R^3$ represents straight-chain or branched alkyl having up to 3 carbon atoms, and $R^4$ represents straight-chain, branched or cyclic alkyl which has up to 4 carbon atoms and is optionally substituted by carboxyl or $C_1$-$C_3$-alkoxycarbonyl.

3. A dihydropyridinelactol or salt thereof according to claim 1, in which $R_1$ represents a phenyl radical which is optionally substituted by nitro, chlorine, trifluoro-$C_1$-$C_3$-alkyl or $C_1$-$C_3$-alkyl, $R_2$ represents a $C_1$-$C_4$-alkyl radical which is optionally substituted by $C_1$- or $C_2$-alkoxy, $R_3$ represents a $C_1$-$C_3$-alkyl group, and $R_4$ represents a $C_1$-$C_4$-alkyl group.

4. A compound according to claim 1, wherein such compound is isopropyl 4-(2-chlorophenyl)-1-ethyl-7-hydroxy-2-methyl-5-oxo-1,4,5,7-tetrahydrofuro[3,4-b]pyridine-3-carboxylate of the formula

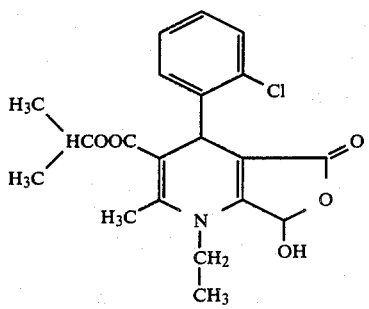

or a physiologically acceptable salt thereof.

5. A compound according to claim 1, wherein such compoud is ethyl 4-(2-chlorophenyl)-1-ethyl-7-hydroxy-2-methyl-5-oxo-1,4,5,7-tetrahydrofuro[3,4-bgpyridine-3-carboxylate of the formula

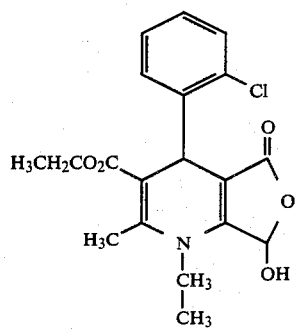

or a physiologically acceptable salt thereof.

6. A compound according to claim 1, wherein such compound is isoproyl 1-ethyol-7-hydroxy-2-2-methyl-4-(2-methylphenyl)-5-oxo-1,4,5,7-tetrahydrofuro[3,4,-b[pyridine -3- carbboxylate of the forumula

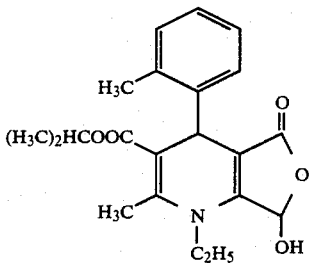

or a physiologically acceptable salt thereof.

7. A compound according to claim 1, wherein such compound is isopropyl 1-ethyl-7-hydroxy-2-methyl-5-oxo-4-(2-trifluromethylphenyl)-1,4,5,7-tetrahydrofuro[3,4-b]-pyridine-3-carboxylate of the formula

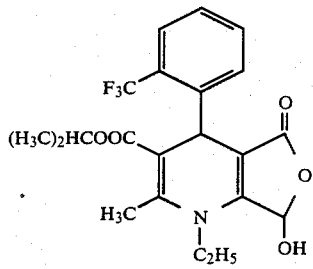

or a physiologically acceptable salt thereof.

8. A compound according to claim 1, wherein such compound is isopropyl 1-ethyl-7-hydroxy-2-methyl-4-(3-nitrophyenyl)-5-oxo-1,4,5,7-tetrahydrofuro[3,4-b]-pyridine -3-carboxylate of the formula

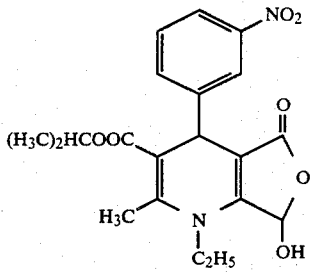

or a physiologically acceptable salt thereof.

9. A blood sugar reducing composition comprising an amount effective therefor of a dihydropyridinelactol or salt thereof according to claim 1 and a diluent.

10. A method of reducing the amount of sugar in the blood of a patient in need thereof which comprises administering to such patient an amount effective therefor of a dihydropyridinelactol or salt thereof according to claim 1.

11. The method according to claim 10, wherein such compound is
isopropyl 4-(2-chlorophenyl)-1-ethyl-7-hydroxy-2-methyl-5-oxo-1,4,5,7-tetrahydrofuro[3,4-b]pyridine-3-carboxylate,
ethyl 4-(2-chlorophenyl-1-ethyl-7-hydroxy-2methyl-5-oxo-1,4,5,7-tetrahydrofuro[3,4-b]pyridine-3-carboxylate, isopropyl 1-ethyl-7-hydroxy-2-methyl-4-(2-methylphenyl)-5-oxo-1,4,5,7-tetrahydrofuro [3,4-b]pyridine-3 -carboxylate,
isopropyl 1-ethyl-7-hydroxy-2-methyl-5-oxo-4-(2-trifluoromethylphenyl)-1,4,5,7-tetrahydrofuro [3,4b]-pyridine-3-carboxylate or
isopropyl 1-ethyl-7-hydroxy-2-methyl-4-(3-nitrophenyl)-5-oxo-1,4,5,7-tetrahydrofuro [3,4-b]-pyridine-3-carboxylate,
or a physiologically acceptable salt thereof.

* * * * *

UNITED STATES PATENT AND TRADEMARK OFFICE
CERTIFICATE OF CORRECTION

PATENT NO. : 4,721,719

DATED : January 26, 1988

INVENTOR(S) : Siegfried Goldmann, et al.

It is certified that error appears in the above-identified patent and that said Letters Patent is hereby corrected as shown below:

| | |
|---|---|
| Col. 1, line 37 | Delete "di-$C_1$-$C_1$-" and substitute --di-$C_1$-$C_3$-- |
| Col. 1, line 40 and Col. 10, line 30 | Delete "N-$C_1$-$C_1$-" and substitute --N-$C_1$-$C_3$-- |
| Col. 1, line 50 | Delete "able" |
| Col. 2, line 6 | Delete "trifluoro-$C_1$-$C_1$" and substitute --trifluoro-$C_1$-$C_3$- -- |
| Col. 2, line 7 and Col. 2, line 10 | Delete "$C_1$-$C_1$-" and substitute --$C_1$-$C_3$- -- |
| Col. 4, lines 34-35 | Delete "tert-.butyllithium" and substitute --tert.-butyllithum-- |
| Col. 8, lines 67-68 | Delete "42/50%);20%),-42/50%);" |
| Col. 9, line 4 | Delete "1-ethyl-7hydroxy-" and substitute --1-ethyl-7-hydroxy- -- |
| Col. 9, line 32 | Delete "(3-nitrophenyL)" and substitute --(3-nitrophenyl)-- |
| Col. 10, line 31 | After "oxygen," insert --and-- |
| Col. 11, line 19 | Delete "bgpyridine-" and substitute --b/pyridine- -- |
| Col. 11, line 38 | Delete "1-ethyol-7-hydroxy-2-2-" and substitute --1-ethyl-7-hydroxy-2- -- |

UNITED STATES PATENT AND TRADEMARK OFFICE
CERTIFICATE OF CORRECTION

PATENT NO. : 4,721,719

DATED : January 26, 1988

INVENTOR(S) : Siegfried Goldmann, et al.

It is certified that error appears in the above-identified patent and that said Letters Patent is hereby corrected as shown below:

| | |
|---|---|
| Col. 11, line 40 | Delete "b/pyridine-3-carboxylate of the forumula" and substitute --b/pyridine-3-carboxylate of the formula-- |
| Col. 12, line 46 | Delete "2methyl-" and substitute --2-methyl- -- |
| Col. 12, line 48 | Start new paragraph with "ispropyl" |

Signed and Sealed this

Twelfth Day of July, 1988

Attest:

DONALD J. QUIGG

Attesting Officer

Commissioner of Patents and Trademarks